(12) United States Patent
Hirami et al.

(10) Patent No.: US 10,145,858 B2
(45) Date of Patent: Dec. 4, 2018

(54) AUTOMATIC ANALYZING APPARATUS

(71) Applicant: HITACHI HIGH-TECHNOLOGIES CORPORATION, Tokyo (JP)

(72) Inventors: Kenichi Hirami, Tokyo (JP); Kazuhiro Nakamura, Tokyo (JP)

(73) Assignee: HITACHI HIGH-TECHNOLOGIES CORPORATION, Tokyo (JP)

( * ) Notice: Subject to any disclaimer, the term of this patent is extended or adjusted under 35 U.S.C. 154(b) by 0 days.

(21) Appl. No.: 15/328,104

(22) PCT Filed: Jul. 17, 2015

(86) PCT No.: PCT/JP2015/070469
§ 371 (c)(1),
(2) Date: Jan. 23, 2017

(87) PCT Pub. No.: WO2016/017442
PCT Pub. Date: Feb. 4, 2016

(65) Prior Publication Data
US 2017/0219617 A1    Aug. 3, 2017

(30) Foreign Application Priority Data
Jul. 31, 2014  (JP) ................. 2014-155677

(51) Int. Cl.
G01N 35/02    (2006.01)
G01N 35/04    (2006.01)
G01N 35/00    (2006.01)

(52) U.S. Cl.
CPC ....... *G01N 35/026* (2013.01); *G01N 35/0095* (2013.01); *G01N 35/04* (2013.01);
(Continued)

(58) Field of Classification Search
None
See application file for complete search history.

(56) References Cited

U.S. PATENT DOCUMENTS 5,876,670 A    3/1999 Mitsumaki et al.
6,444,171 B1   9/2002 Sakazume et al.
(Continued)

FOREIGN PATENT DOCUMENTS

CN    101470125 A    7/2009
CN    102292645 A    12/2011
(Continued)

OTHER PUBLICATIONS

Hawker, CD. Laboratory Automation: Total and Subtotal. Journal for Clinics in Laboratory Medicine; 27 (2007) p. 749-770 (Year: 2007).*
(Continued)

*Primary Examiner* — Benjamin R Whatley
(74) *Attorney, Agent, or Firm* — Volpe and Koenig, P.C.

(57) ABSTRACT

An automatic analyzing apparatus capable of obtaining an analysis result of a specimen high in urgency in a shorter time is provided. When a first rack 50 is present in a sampling line 103 and an analysis request for a second rack higher in the degree of urgency for analysis than the first rack 50 is detected, a control unit unloads the first rack 50 onto a transport line 100 through a return line 102, allows the first rack 50 to stand by at a rack standby position 120 on a transport line 101 between a loading line 101 and the return line 102 under control, and loads the second rack from the transport line 101 onto the sampling line 103 through the loading line 101 and transports the second rack to the dispensing position 111 under control while allowing the first rack 50 to stand by.

6 Claims, 19 Drawing Sheets

(52) U.S. Cl.
CPC ........... *G01N 2035/0094* (2013.01); *G01N 2035/0412* (2013.01); *G01N 2035/0462* (2013.01); *G01N 2035/0465* (2013.01)

(56) References Cited

U.S. PATENT DOCUMENTS

| | | | |
|---|---|---|---|
| 7,842,237 B1 | 11/2010 | Shibuya et al. | |
| 2004/0186360 A1* | 9/2004 | Suzuki | G01N 35/026 600/310 |
| 2009/0162247 A1 | 6/2009 | Tokieda et al. | |
| 2011/0271773 A1 | 11/2011 | Komatsu et al. | |
| 2012/0036944 A1* | 2/2012 | Chida | G01N 35/00613 73/863.01 |
| 2012/0294765 A1 | 11/2012 | Watabe et al. | |
| 2014/0294699 A1* | 10/2014 | Akutsu | G01N 35/04 422/551 |

FOREIGN PATENT DOCUMENTS

| | | |
|---|---|---|
| CN | 102725641 A | 10/2012 |
| JP | 09-043249 A | 2/1997 |
| JP | 10-019899 A | 1/1998 |
| JP | 2000-046842 A | 2/2000 |
| JP | 2000-105246 A | 4/2000 |
| JP | 2001-004639 A | 1/2001 |
| JP | 2009-008552 A | 1/2009 |
| JP | 2012-194197 A | 10/2012 |
| WO | 01/051929 A1 | 7/2001 |
| WO | WO-2013099538 A1 * | 7/2013 ............ G01N 35/04 |
| WO | 2013/151920 A1 | 10/2013 |

OTHER PUBLICATIONS

International Search Report, PCT/JP2015/070469, dated Oct. 20, 2015, 2 pgs.

Office Action for corresponding CN Application.

Extended European Search Report dated Feb. 14, 2018 for the European Application No. 15828243.4.

* cited by examiner

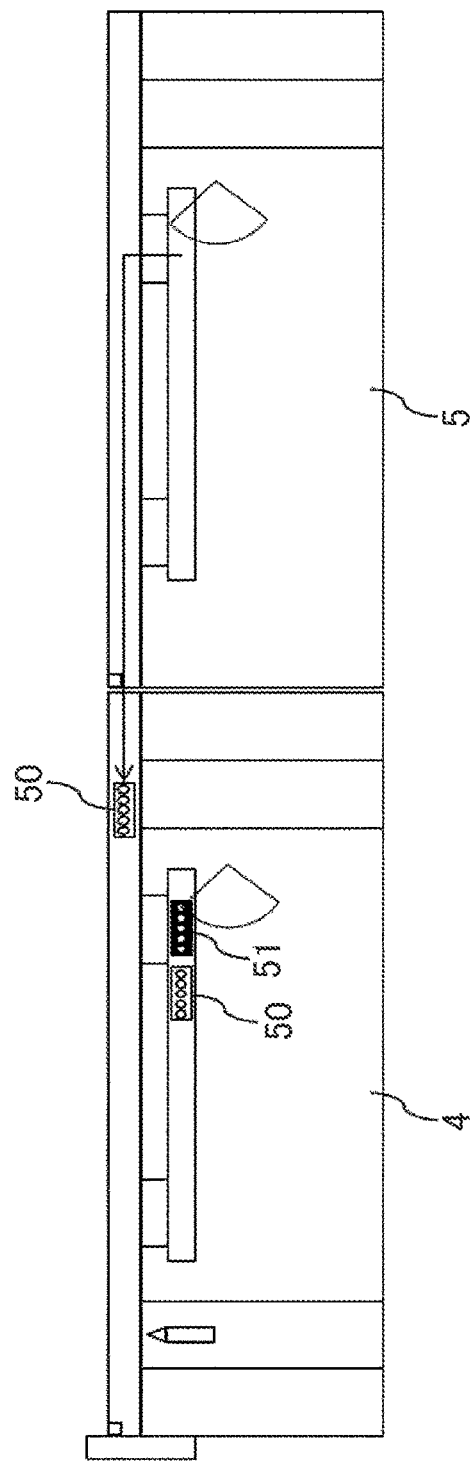

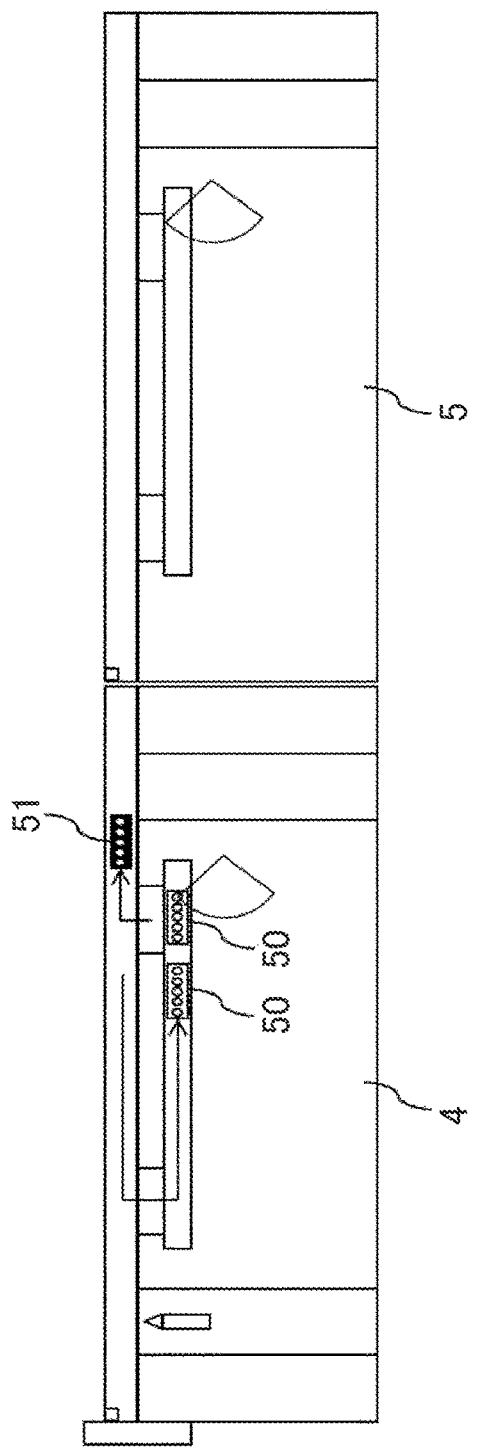

AUTOMATIC ANALYZING APPARATUS

TECHNICAL FIELD

The present invention relates to an automatic analyzing apparatus for performing quantitative and qualitative analysis of biological samples such as blood and urine, and more particularly to an automatic analyzing apparatus having a transport device for transporting a sample container to an analyzing device.

BACKGROUND ART

An automatic analyzing apparatus that automatically performs quantitative and qualitative analyses of biological samples such as blood and urine are widespread mainly in large hospitals and clinical laboratory centers where a large number of patient specimens need to be processed in a short period of time, and large, medium and small automatic various analyzing apparatuses have been developed. Particularly, in the case of a large-sized apparatus which analyzes a large number of specimens, a plurality of specimen containers containing specimens are transported in a state of being held by a holder called a specimen rack to multiple analyzing devices through a transport line, and an inspection technician merely inserts the rack into a specimen rack insertion slot to automatically performs the analysis until an output of the analysis result.

CITATION LIST

Patent Literature

Patent Literature 1: Japanese Unexamined Patent Application Publication No. 2012-194197

SUMMARY OF INVENTION

Technical Problem

Among the specimens, there is an "urgent specimen", which is a specimen with high urgency, which is urgent for analysis as compared with other specimens. Such an urgent specimen is distinguished from other specimens that are comparatively in no hurry to perform analysis, i.e., "general specimens". The urgent specimen needs to be analyzed preferentially compared to the general specimens. An automatic analyzing apparatus capable of obtaining the analysis result of the "urgent specimen" in a shorter time is provided.

In the automatic analyzing apparatus disclosed in Patent Literature 1 described above, when the urgent specimen is inserted into the rack, the rack is moved to a mechanism at a temporary standby position, the urgent specimen dispensing is interrupted, the dispensing is performed, and the urgent specimen can be rapidly analyzed. Therefore, there is a need to add a buffering mechanism to the analyzing apparatus for the standby position.

Further, since the rack having the urgent specimen is carried into the analyzing device via the buffering mechanism, it is desirable to rapidly complete the operation of the buffering mechanism for putting the rack into a temporary standby state. However, when the operation of the buffering mechanism cannot be completed rapidly, there is a problem that the rack of the urgent specimen cannot be carried into the analyzing device.

Solution to Problem

The representative invention of the present application will be described below.

An automatic analyzing apparatus includes: a transport line for transporting a rack on which a sample container containing a sample is mounted; a sampling line for transporting the rack on the transport line to a dispensing position where the sample is dispensed; an analysis unit that dispenses the sample from the rack transported to the dispensing position and analyzes the sample; and a control unit that controls the transport line and the sampling line, in which the control unit loads the rack from the transport line onto the sampling line through a loading line, and after the dispensing at the dispensing position has been completed, the control unit unloads the rack from the sampling line onto the transport line through a return line under control, when a first rack is present in the sampling line and an analysis request for a second rack higher in the degree of urgency for analysis than the first rack is detected, the control unit unloads the first rack onto the transport line through the return line, and allows the first rack to stand by at a rack standby position on the transport line between the loading line and the return line under control, and the control unit loads the second rack from the transport line onto the sampling line through the loading line and transports the second rack to the dispensing position while the first rack is allowed to stand by.

With the above configuration, even when a mechanism such as a standby portion is present, the rack having the urgency is allowed to rapidly reach the dispensing portion on the sampling line to enable analysis. Also, in the present invention, the problem can be solved without any addition of the mechanism portion such as the standby portion. In that case, the problem can be solved without any increase in a size and cost of the apparatus.

Advantageous Effects of Invention

The rack having the urgency is allowed to rapidly reach the dispensing position on the sampling line to enable analysis. Also, in the present invention, the rack having the urgency is allowed to rapidly reach the dispensing position on the sampling line to enable analysis without any addition of the mechanism portion such as the standby portion. In that case, the problem can be solved without any increase in a size and cost of the apparatus.

BRIEF DESCRIPTION OF DRAWINGS

FIG. 18 is a diagram of the schematic control flow according to the third embodiment.

FIG. 19 is a diagram of the schematic control flow according to the third embodiment.

DESCRIPTION OF EMBODIMENTS

Hereinafter, a specimen dispensing device, a specimen dispensing method, and a dispensing device according to embodiments of the present invention will be described in detail.

Figure 1:
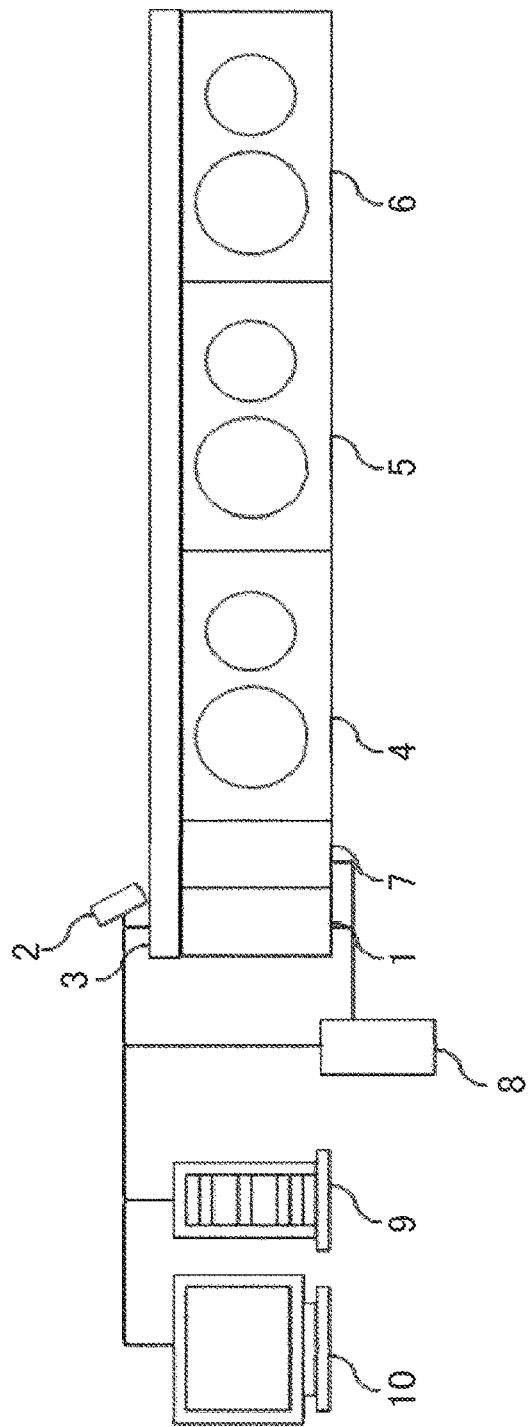
FIG. 1 is an overall schematic diagram of an automatic analyzing system.

FIG. 1 is an overall schematic diagram of an automatic analyzing system according to an embodiment of the present invention.

An automatic analyzing apparatus according to the present embodiment includes a specimen rack loading unit 1, an ID reading unit 2, a transport line 3, analysis modules 4, 5, and 6, a specimen rack recovery unit 7, and an overall management computer (control unit) 8.

The specimen rack loading unit 1 is a portion for loading multiple specimen racks each for holding multiple specimens (hereinafter also referred to as "samples"). The analysis modules 4, 5, and 6 are aligned along a transport line 3, and are detachably connected to the transfer line 3. The number of analysis modules can be arbitrarily set, and the present embodiment shows a case where the number of modules is three.

The transport line 3 transports the specimen racks from the specimen rack loading unit 1 to the analysis modules 4, 5, and 6 according to an analysis request, or transports the specimen racks whose analysis by the analysis modules 4, 5, and 6 has been completed or the specimen racks requested for the analysis to the specimen rack recovery unit 7.

The specimen rack loading unit 1 includes the overall management computer 8 that performs necessary controls within the specimen rack loading unit 1, the ID reading unit 2, the transport line 3, and the specimen rack recovery unit 7. The overall management computer 8 is further connected with the operation unit 9 that inputs necessary information and the display unit 10 that displays the analysis result.

Each specimen held by the specimen rack has a specimen ID indicative of an attribute information (acceptance number, patient name, request analysis item, and so on) on the specimen, and each specimen rack has a rack ID indicative of rack identification information such as a rack number or the like. The specimen racks placed in the specimen rack loading unit 1 is transported by the transport line 3, and when each specimen rack moves to the transport line 3, the specimen ID and the specimen rack ID are read by the ID reading unit 2 and sent to the overall management computer 8.

The overall management computer 8 determines which analysis module to be executed from the requested analysis item, on the basis of the attribute information. The transport line 3 transports the specimen racks to the determined analysis module, and the analysis operation is implemented in the subject analysis module.

In this situation, the transport line 3 identifies specimen racks different in a shape and transports the identified specimen racks to the analysis modules 4, 5, and 6. The transport line 3 are controlled by the overall management computer (control unit) 8.

The embodiment of the present invention shows an example in which four specimen racks can be installed on the sampling line. In addition, the present embodiment shows an example of the rack on which multiple sample containers, for example, five sample containers (hereinafter also referred to as "sample container") containing the samples (hereinafter referred to as "samples") can be mounted. However, the rack may hold one sample container.

Figure 2:
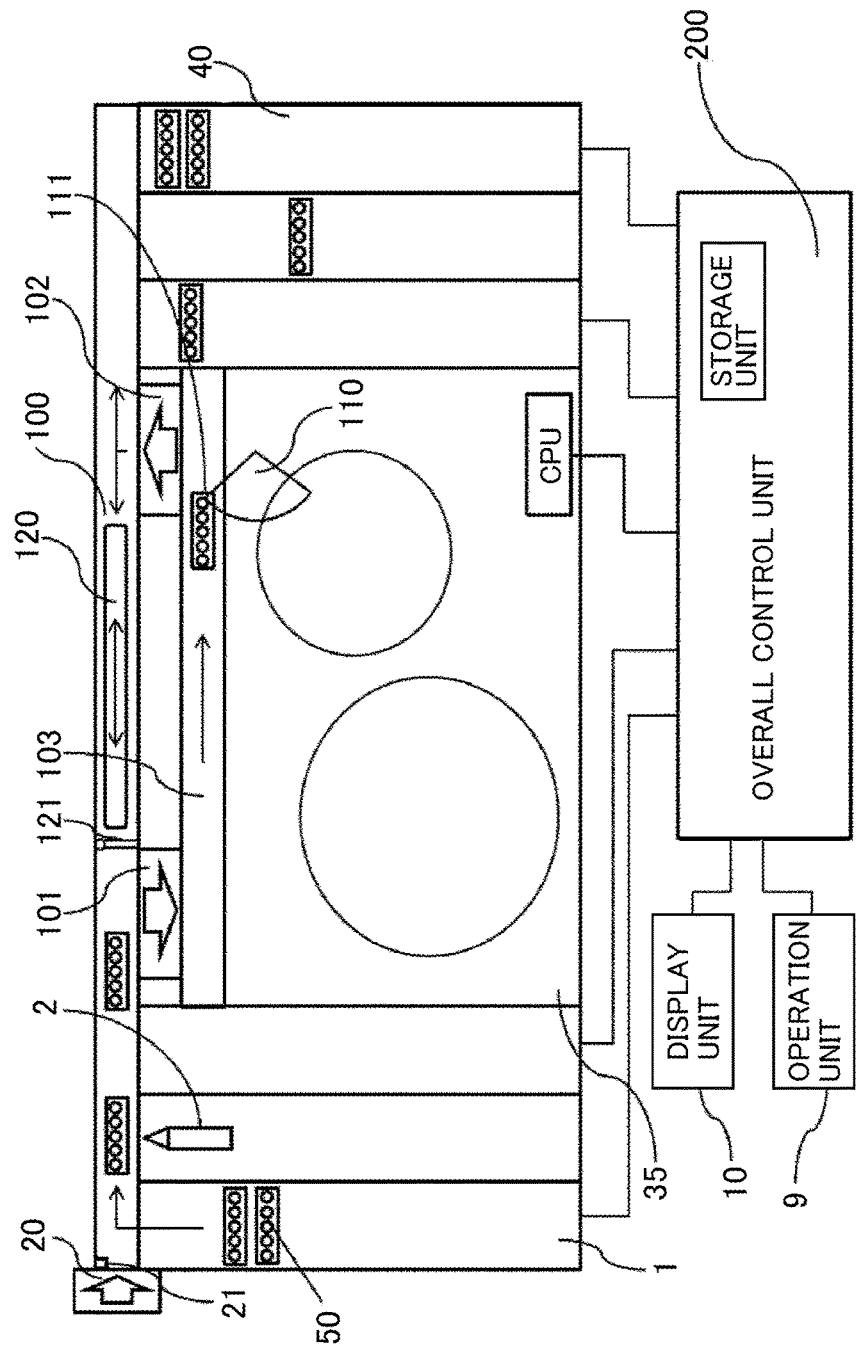
FIG. 2 is a schematic diagram of an automatic analyzing apparatus module.

FIG. 2 is a schematic configuration diagram of one of the analysis modules in the automatic analyzing apparatus. In other words, FIG. 2 illustrates an example of the automatic analyzing apparatus including one analysis module. As illustrated in FIG. 2, the automatic analyzing apparatus includes the specimen rack loading unit 1, a recovery unit 40 for the analyzed racks, the ID reading unit 2 that reads information on the racks inserted from the specimen rack loading unit 1, an urgent rack insertion unit 20, an urgent rack detection sensor 21, a transport line 100 for transporting the racks to the respective analysis mechanisms, a dispensing device 110 for dispensing the specimens of each rack, a sampling line 103 including a dispensing position 111 at which the dispensing device performs the dispensing, a loading line 101 that moves the racks from the transport line 100 to the sampling line 103, a return line 102 that moves the racks from the sampling line 103 to the transport line 100, and an general control unit (control unit) 200 that controls the movement of the racks. The general control unit (hereinafter also referred to merely as "control unit") 200 corresponds to the overall management computer 8, and performs a line control of the transport line 100 and the sampling line 103. In addition, the sampling line 103 can transport the racks on the transport line 100 to the dispensing position 111 by the aid of the general control unit (control unit) 200.

The sampling line 103 and the transport line 100 of the automatic analyzing apparatus each have a space in which the multiple specimen racks can be arranged. In particular, a rack standby position 120 for allowing the racks to stand by is disposed between on the transport line 100 between the loading line 101 and the return line 102, at which the racks temporarily can stand by. Also, a rack stopper 121 is provided to stop the movement of the racks at the rack standby position 120 and stop the racks. The transport line 100 is a belt conveyor, and the rack stopping mechanism 121 physically stops the racks to be transported by the belt conveyor, and allows the racks to stand by at the rack standby position 120. The overall control unit (control unit) 200 can allow the racks to stand by at the rack standby position 120 while controlling the transport line 100 or the rack stopper 121.

Even without the rack stopper 121, the racks can be allowed to stand by at the rack standby position 120 by precisely controlling the transport line 100. However, with the provision of the rack stopper 121, the racks can be allowed to more easily stand by at the rack standby position 120. In addition, the transport line 100 can be bidirectionally moved so as to be able to transport the racks to either the rack recovery unit 40 or the rack standby unit 120.

In addition, the automatic analyzing apparatus is equipped with an analysis unit 35 including the dispensing device 110, and the analysis unit 35 dispenses the specimens from the racks transported to the dispensing position 111 and analyzes the specimens. The analysis unit 35 further includes a reagent container holding unit that holds multiple reagent containers for storing reagents for analysis, a reaction disk that holds multiple reaction containers for mixing the reagent and the sample together, a reagent dispensing mechanism for dispensing reagents from a reagent container to reaction containers, and an optical system for measuring an absorbance by irradiating a mixed solution in the reaction vessel with a light, and the analysis unit 35 calculates the concentration of a predetermined component contained in the sample on the basis of an absorbance of the mixed solution measured by the optical system. However, the analysis unit described above is directed to an analysis unit for biochemical items, and the analysis unit for immune items includes a different mechanism. However, since the contents of the analysis unit are not essential matters, its detailed description will be omitted in the present specification. In other words, the analysis unit includes various analyzing devices.

Normally, the general control unit (control unit) 200 loads the racks from the transport line 100 to the sampling line 103 through the loading line 101, and after dispensing at the dispensing position 111 has been completed, the general control unit (control unit) 200 unloads the racks from the sampling line 103 through the return line 102 to the transport line 100 under control. The dispensing device 111 dispenses the samples from the sample containers mounted on each rack one after another, and the analysis unit 35 analyzes those samples. In order to enhance a dispensing efficiency of the dispensing device 111, the multiple racks waiting for dispensing are allowed to wait in front of the dispensing position 111 on the sampling line 103. As described above, in the following example, four racks can be loaded with the inclusion of the dispensing position 111.

Incidentally, the specimens described above include an urgent specimen 51, which is a specimen with a high urgency, being analyzed more rapidly than other specimens. Such an urgent specimen is distinguished from other specimens, which are relatively unhurried in analysis, that is, general specimens 50.

The urgent specimen needs to be analyzed preferentially compared to the general specimens. In order to distinguish such an urgent specimen from the general specimen, information indicative of "specimen classification" which is a classification for identifying the specimen is attached to, for example, a container (not shown) containing the specimen or the like. The automatic analyzing apparatus can read information indicative of the specimen classification of each specimen from the container and reflect the read specimen classification on an analysis work.

As in the automatic analyzing apparatus described above, in the analyzing device that installs the multiple specimens on the line and analyzes the specimens, in the case where the general specimens have already been installed on the sampling line as "installed specimens", when an urgent specimen (additional specimen) suddenly occurs for the urgent specimen (additional specimen) that is more urgent among the urgent specimens, until the analysis of the general specimens (installed specimens) already installed on the sampling line is completed, the subject urgent specimen (additional specimen) cannot be analyzed. In the present invention, the analysis result of the highly urgent specimen can be obtained in a shorter time against this problem.

First Embodiment

A control flow of the rack movement when the urgent specimen is inserted into an automatic device is illustrated in FIGS. 3 to 11. FIG. 12 illustrates a flowchart of FIGS. 3 to 11.

Figure 3:
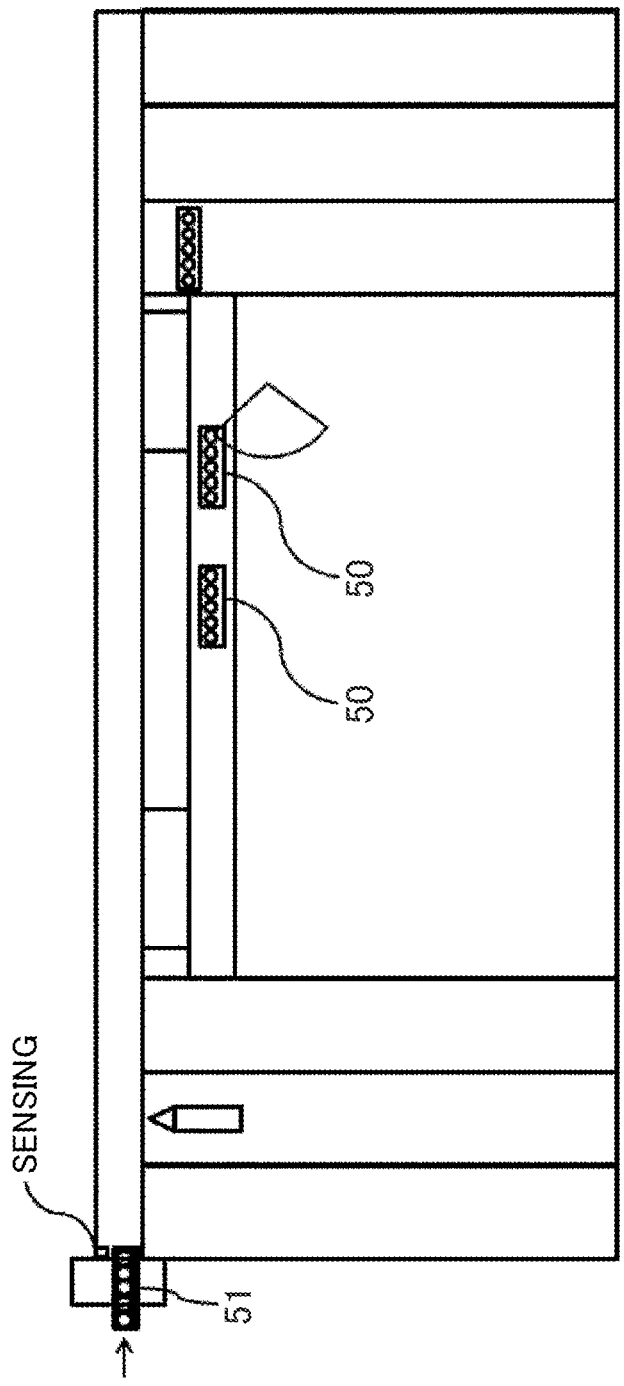
FIG. 3 is a diagram of a schematic control flow according to a first embodiment.

As illustrated in FIG. 3, the normal specimens are moved from each specimen rack, and specimen label information is read by the ID reading unit 2 such as a barcode reader. On the other hand, when the specimen is a specimen with high urgency, the specimen is inserted from a dedicated specimen loading port, and the sensor 51 which senses loading senses the rack inserted from the dedicated specimen loading port (S100 in FIG. 12). In other words, the control unit detects an urgent specimen analysis request in response to the sensing.

When the sensor 51 senses the rack, the dispensing of the general specimens, which are "installed specimens" installed at dispensing position 111, is interrupted once. In this situation, a progress situation of the stopped dispensing of the specimens is stored in a storage unit of the overall control unit 200. At the same time, the supply of the new general specimen rack from the specimen rack loading unit 1 to the transport line 100 is interrupted (S 110 in FIG. 12).

Figure 4:
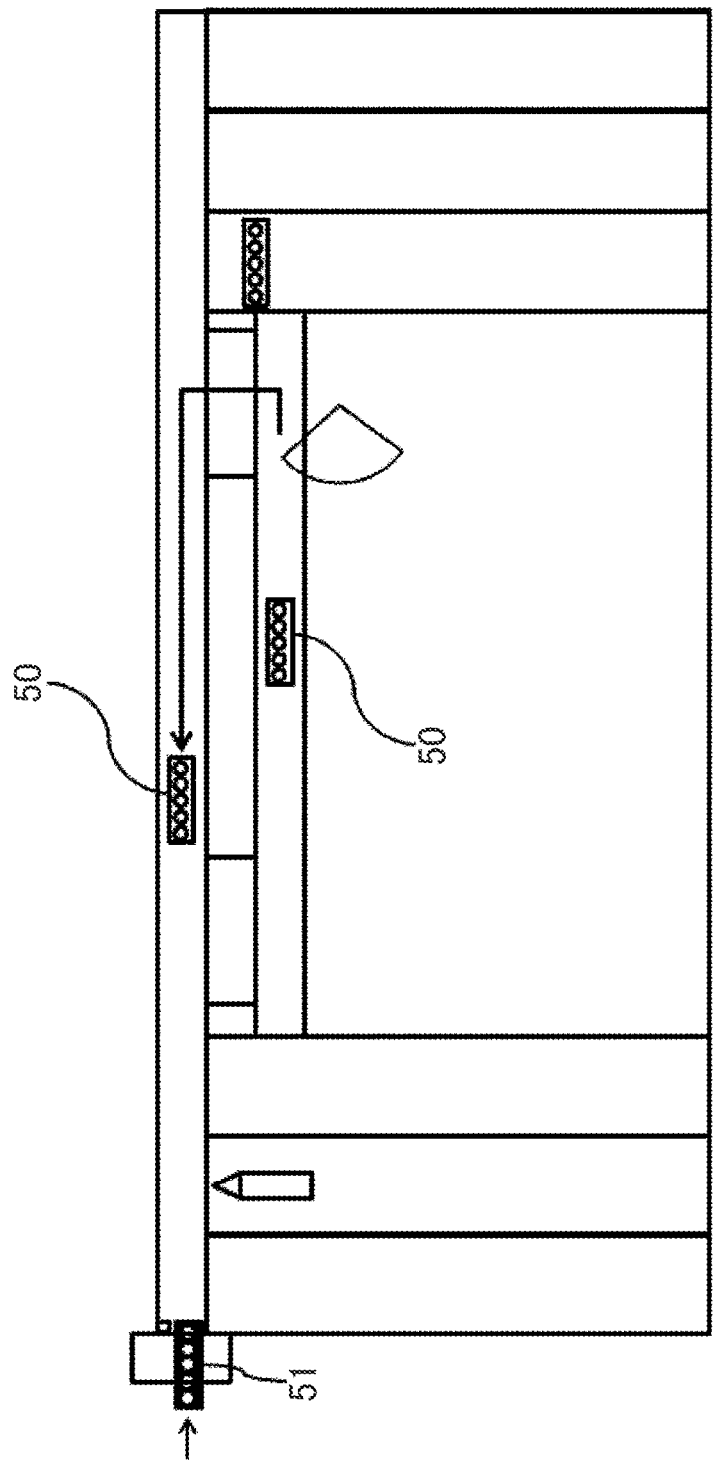
FIG. 4 is a diagram of the schematic control flow according to the first embodiment.

The general specimen racks (hereinafter also referred to as general specimens) whose dispensing has been interrupted move from the sampling line 103 to the return line 102 as illustrated in FIG. 4. The general specimens that have passed through the return line 102 moves to the transport line 100 and moves the general specimens to a side of the loading line 101, thereby moving to the rack standby position 120 that is a place that does not interfere with the movement and dispensing of the urgent specimen racks (hereinafter also referred to as urgent specimens). When the general specimens are transported to the position of the loading line 101, since the transported general specimens interfere with the transport of the urgent specimens to the sampling line 103, the general specimens are transported to a place in front of the loading line 101 and allowed to stand by as shown in the figure.

Figure 5:
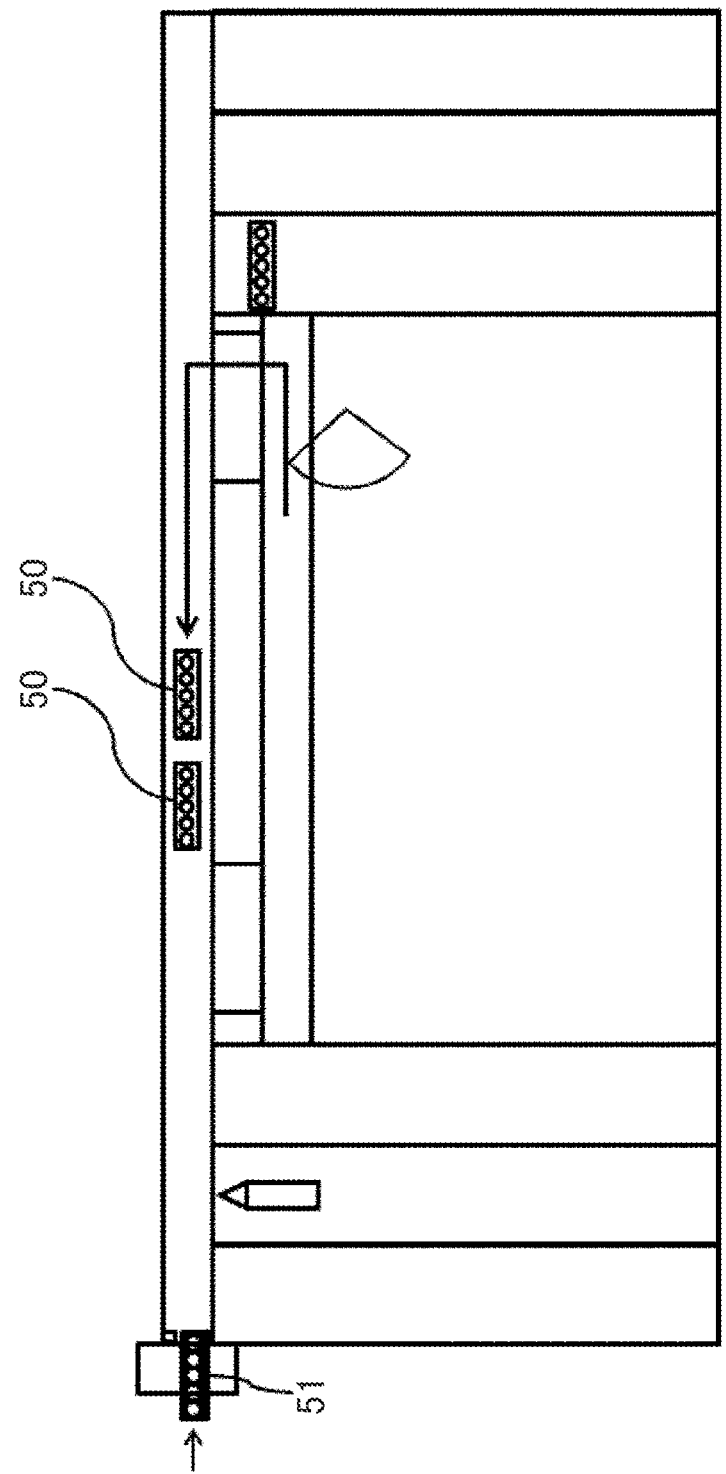
FIG. 5 is a diagram of the schematic control flow according to the first embodiment.

FIG. 5 is a control flow when the other general specimens are installed on the sampling line. When the general specimen rack is installed on the sampling line in addition to the specimens being dispensed, the general specimen rack is sent onto the transport line through the return line 102 in the same manner as that of the rack which has been moved earlier, and the general specimen rack is allowed to stand by at the rack standby position 120 that is a place that does not interfere with the movement and the dispensing of the urgent specimen rack on the transport line (S 120 in FIG. 12).

Figure 6:
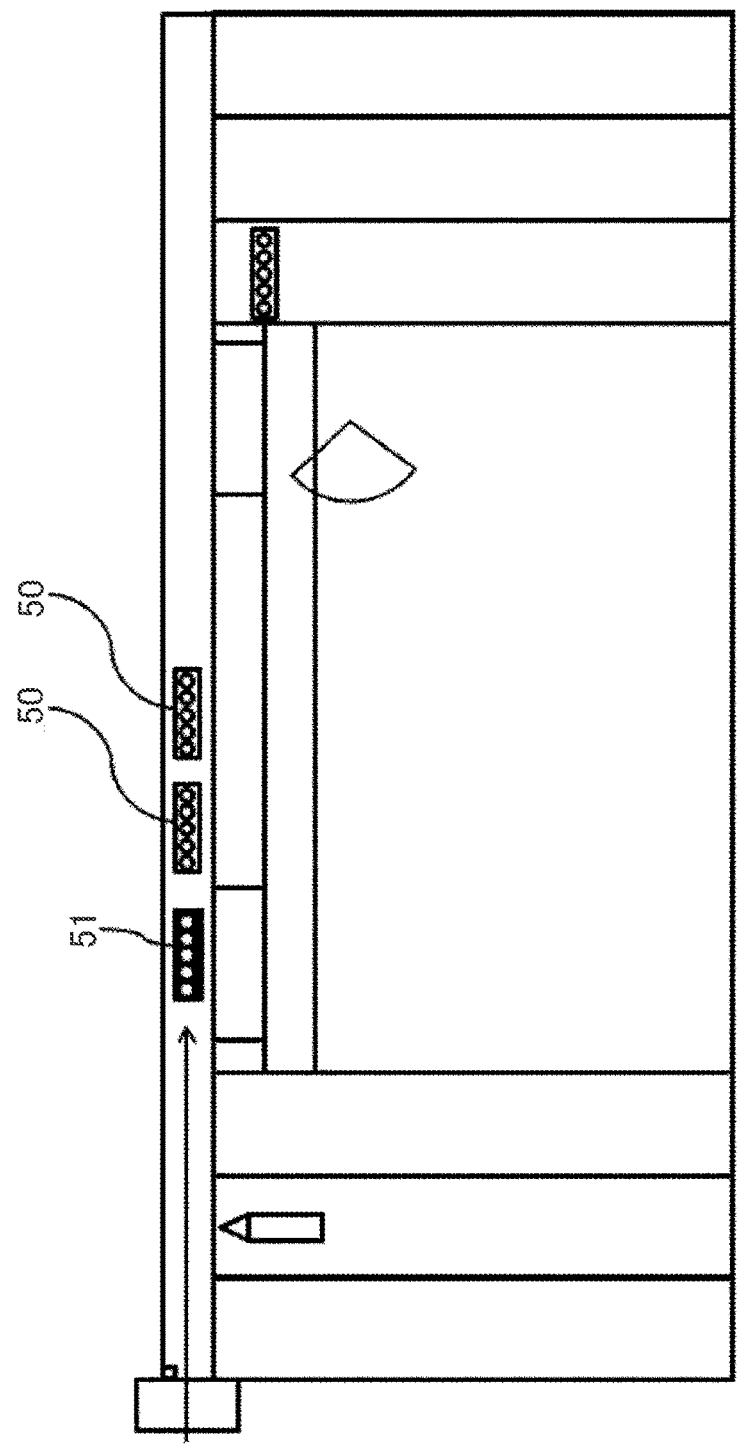
FIG. 6 is a diagram of the schematic control flow according to the first embodiment.
Figure 7:
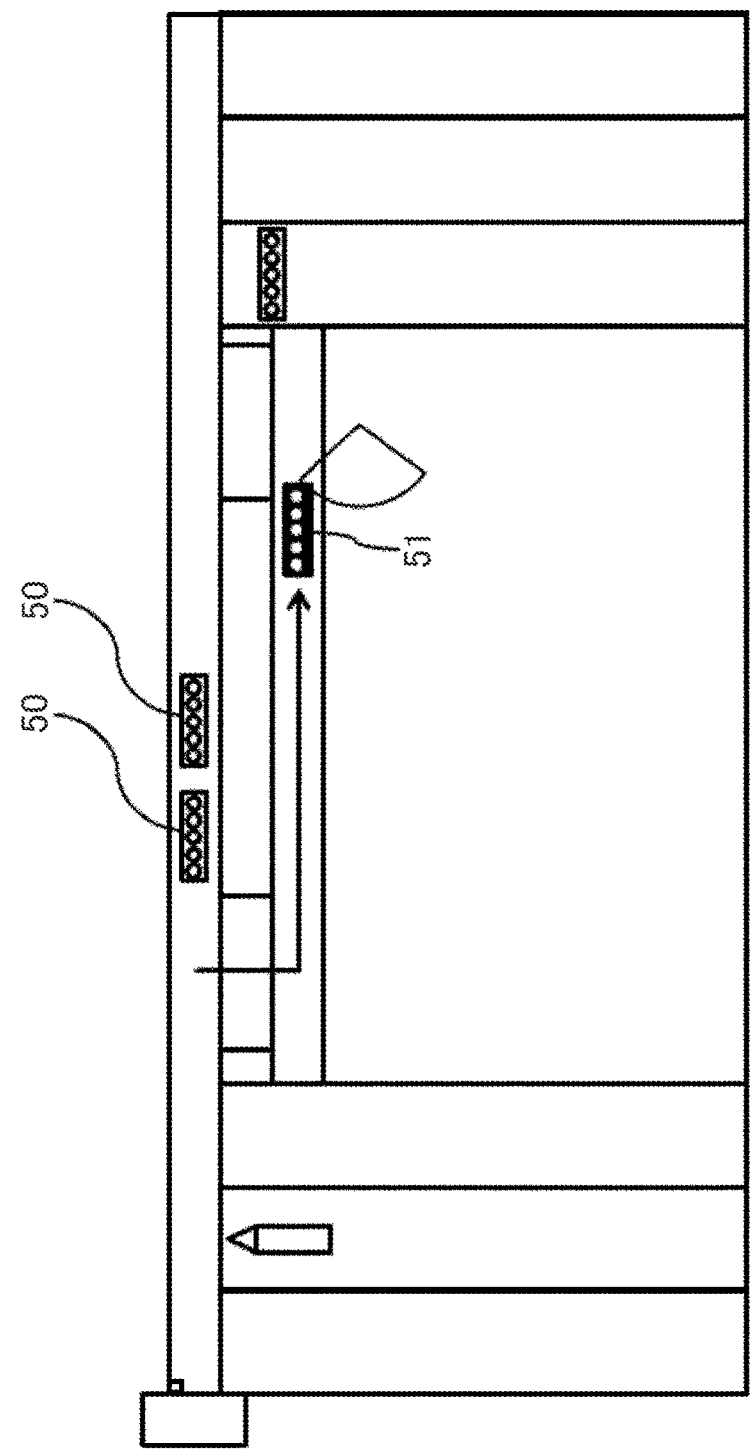
FIG. 7 is a diagram of the schematic control flow according to the first embodiment.

FIGS. 6 and 7 illustrate a rack movement control flow of the emergency specimen. As illustrated in FIG. 4, at the same time when the urgent specimen is inserted into the specimen insertion unit, and starts to retreat from the sampling line of the general specimen to the rack standby position 120, the urgent specimen reaches the sampling line through the loading line as the rack of the normal specimens (S130 in FIG. 12).

As illustrated in FIGS. 4 and 5, the general specimen rack retreats from the sampling sign to the rack standby position 120 of the transport line. For that reason, when the urgent specimen rack reaches the sampling line, the urgent specimen rack reaches the dispensing position 111 of the specimen without the generation of a waiting time, and the dispersing can start (S140 in FIG. 12).

Figure 8:
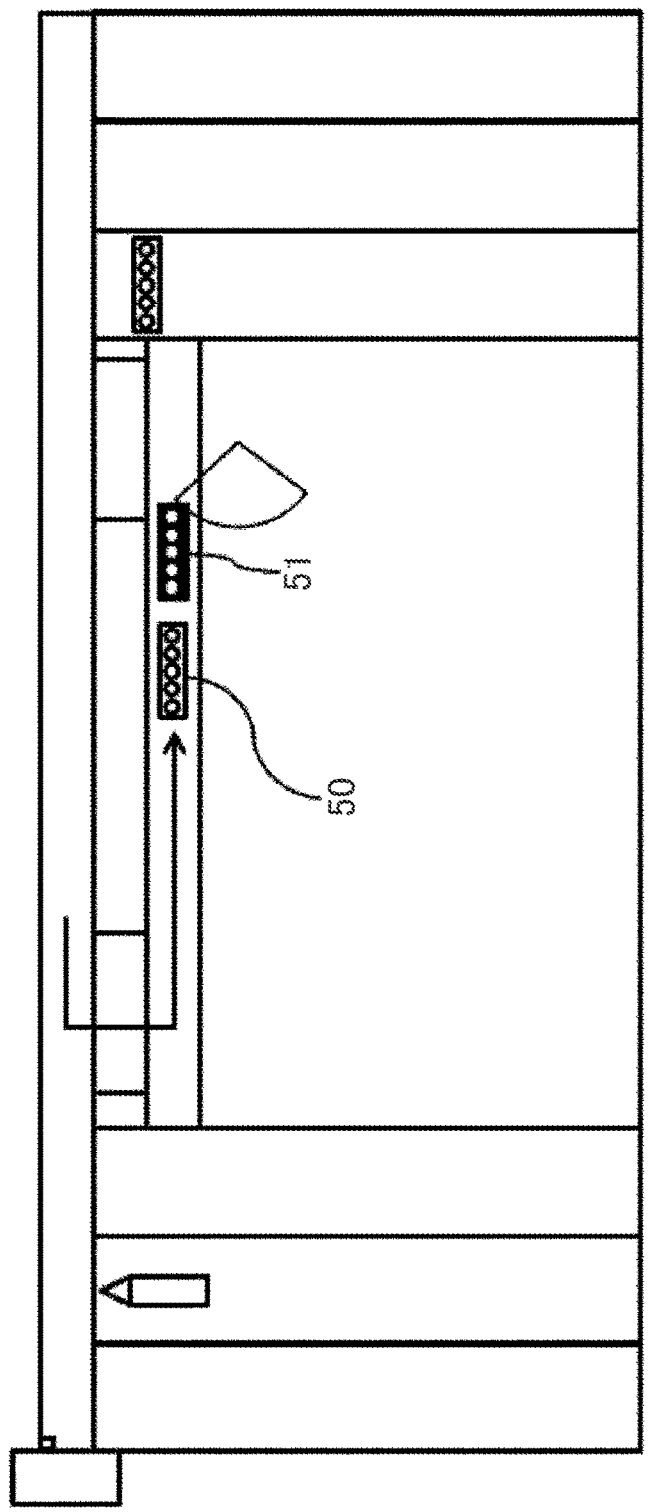
FIG. 8 is a diagram of the schematic control flow according to the first embodiment.

FIG. 8 illustrates a control flow of the general specimen when the urgent specimens start to be dispensed. After the dispensing of the urgent specimen has started, the rack of the general specimens which have been the installed specimens reaches the loading line from the rack standby position 120 through the transport line.

The general specimen rack which has reached the loading line is placed again on the sampling line, and waits until the completion of dispensing of the urgent specimen rack where the dispensing is performed at the dispensing position on the sampling line.

Figure 9:
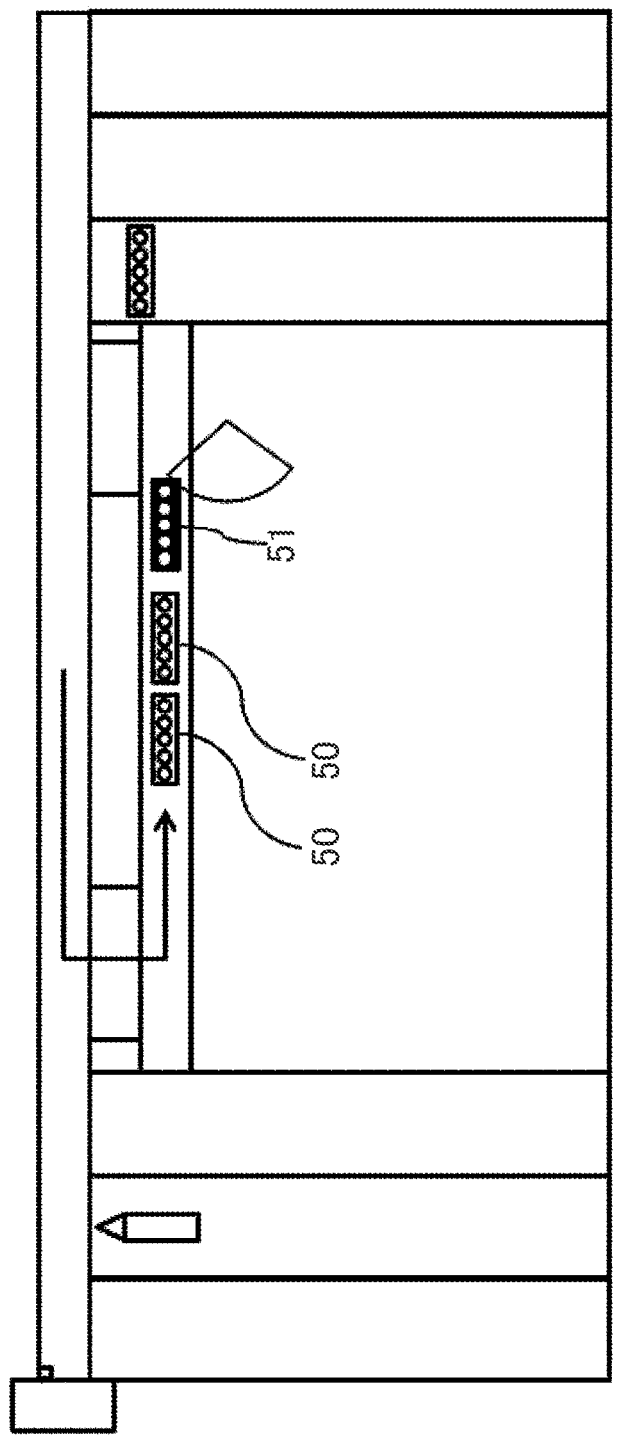
FIG. 9 is a diagram of the schematic control flow according to the first embodiment.

FIG. 9 illustrates a control flow of the general specimens when the rack other than the installed specimens has retreated to the rack standby position 120 of the transport line in FIG. 5. The rack of the general specimens which has retreated to the rack standby position 120 of the transport line reaches the loading line through the transport line.

The general sample racks that reached the loading line are again installed on the sampling line. As with the general sample racks illustrated in FIG. 8, the racks stand by until the dispensing of the urgent specimen racks that are dispensed on the sampling line is completed (S 150 in FIG. 12). Simultaneously with the return of all the racks to the sampling line, the supply and loading of the racks into and from the transport line by the sample rack loading unit 1 are resumed.

Figure 10:
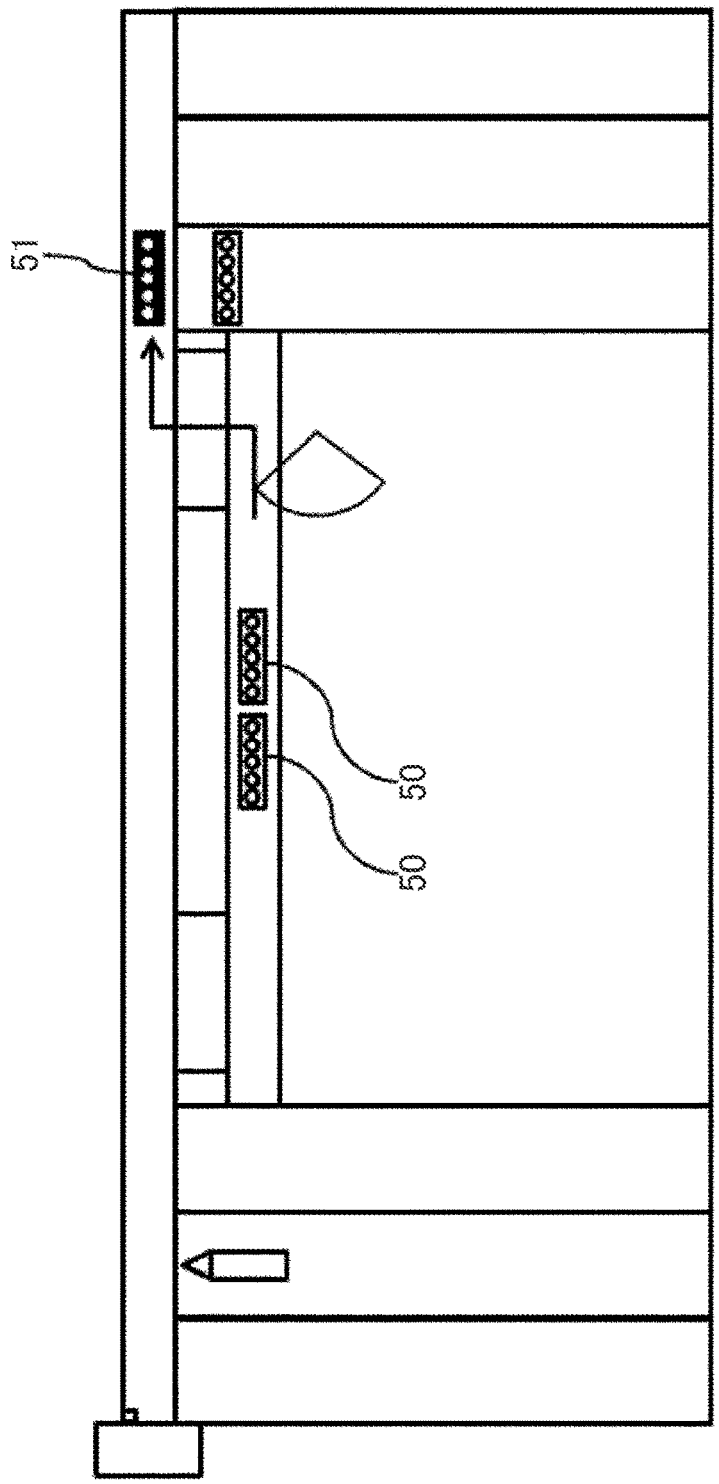
FIG. 10 is a diagram of the schematic control flow according to the first embodiment.
Figure 11:
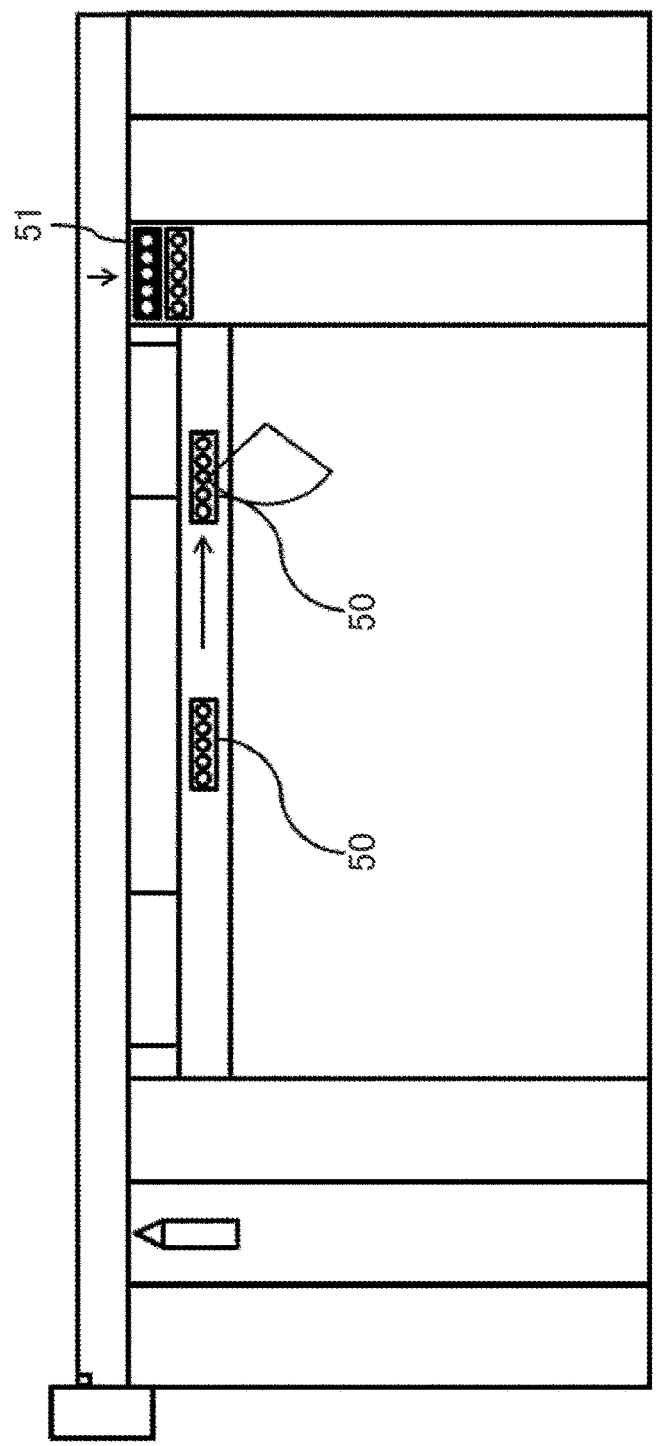
FIG. 11 is a diagram of the schematic control flow according to the first embodiment.
Figure 12:
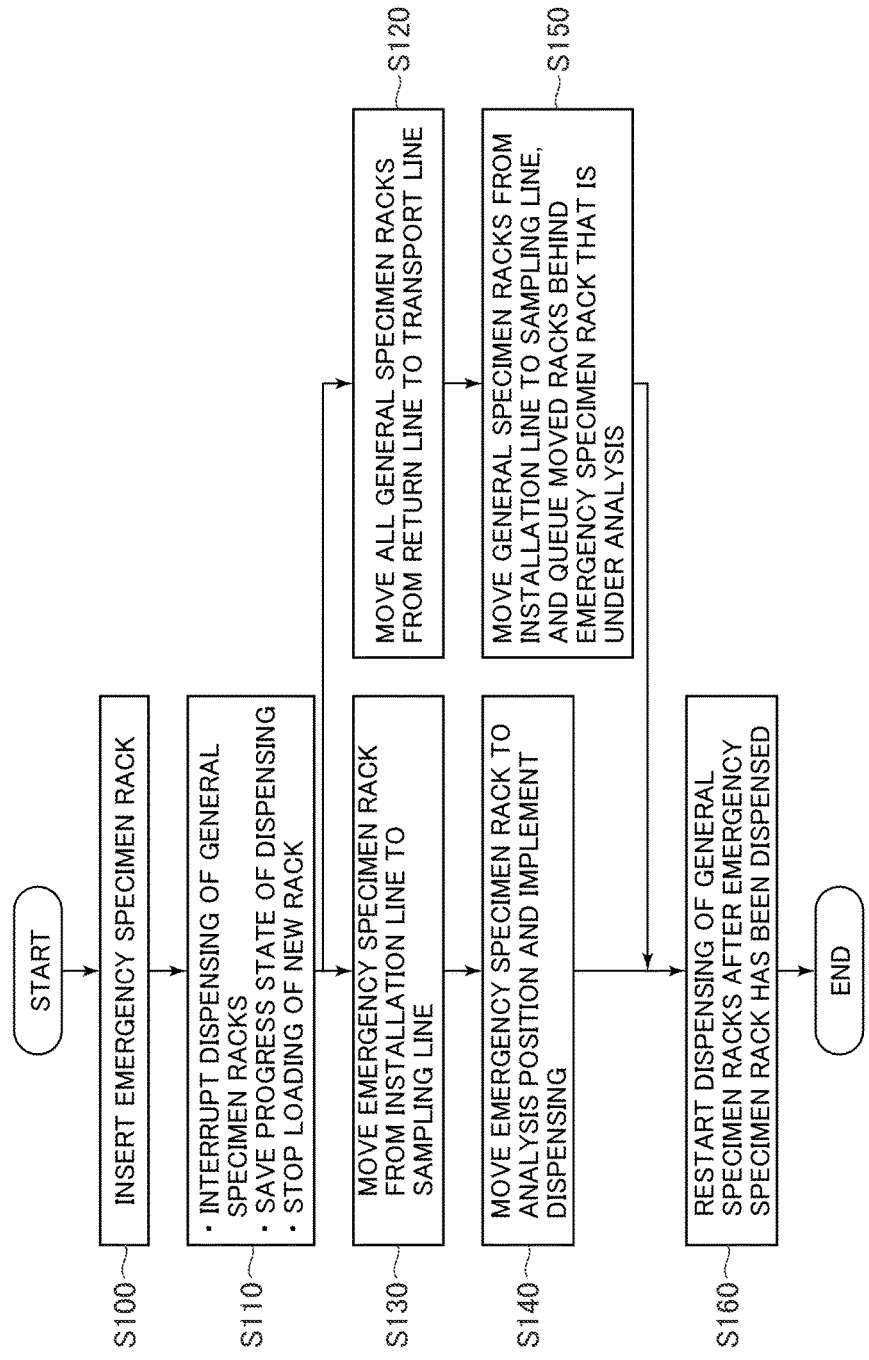
FIG. 12 is a flowchart of the outline according to the first embodiment.

FIGS. 10 and 11 illustrate a control flow of the general specimens after the urgent specimens have been dispensed. When the dispensing of the urgent specimens has been completed, the urgent specimens are transported to the transport line through the return line. The urgent specimens moved to the transport line are moved to another connected module when another analysis is performed. When all the analyses are completed, the respective urgent specimens are moved to the recovery unit of the racks through the transport lines. The present embodiment shows a case in which all the analyses have been completed.

After the rack of the urgent specimens has moved, the rack whose dispensing has been interrupted earlier in FIG. 4 is moved to the dispensing unit. The racks that have reached the dispensing unit restart the dispensing of the specimens from the interruption location stored in the storage unit (S160 in FIG. 12).

As described above, when the general specimens are present in the sampling line and the analysis request for the urgent specimens higher in the degree of urgency for analysis than the general specimens is detected, the control unit unloads the general specimens onto the transport line through the return line, and allows the general specimens to stand by at the rack standby position 120 on the transport line between the loading line and the return line under control, and the control unit loads the urgent specimens from the transport line onto the sampling line through the loading line and transports the urgent specimens to the dispensing position while the general specimens are allowed to stand by. Also, after having loaded the urgent specimens onto the sampling line, the control unit again loads the general specimens from the rack standby position onto the sampling line through the loading line, and transports the general specimens to the dispensing position under control.

Also, when the general specimens are in a rack located at the dispensing position before scheduled dispensing is completed, the control unit interrupts the dispensing of the general specimens and allows the general specimens to stand by at the rack standby position under control.

Also, when a plurality of specimen racks stand by at the rack standby position, the control unit again loads the general specimen racks onto the sampling line from the rack standby position through the loading line, and transports the general specimen racks to the dispensing position, according to a scheduled order of transporting the plurality of general specimen racks to the dispensing position on the sampling line under control.

As illustrated in FIGS. 3 to 11, when the rack standby position 120 on the transport line is set as a temporary retreat place, there is no need to add a mechanism and handling necessary for rapid analysis of the urgent specimens is enabled. In addition, even if there is a buffering mechanism of the racks, the operation of the buffering mechanism is eliminated for the temporary retreat and the operation of this mechanism can be performed for transporting the urgent specimens. Therefore, the racks having the urgency can rapidly reach the dispensing position on the sampling line to enable the analysis. Meanwhile, it is desirable that the rack standby position 120 is not a position included in the buffering mechanism but a position on the line used for transport as with the transport line. In other words, at the rack standby position 120, it is desirable that there is no driving mechanism other than the driving mechanism for transporting the racks to upstream and downstream. This is because the addition of a complicated mechanism causes the apparatus to be upsized or the cost to be increased.

In addition, the handling of the racks in the above flow is implemented with the result that the analysis order of the general specimen racks is not changed. With the above configuration, in the rack of the general specimens, an increase in a time (turnaround lime) since the rack loading until the analysis completion can be suppressed.

Second Embodiment

Next, an example in which an interrupt level of urgent specimens is set on a setting screen on a display unit 10 will be described.

Figure 13:
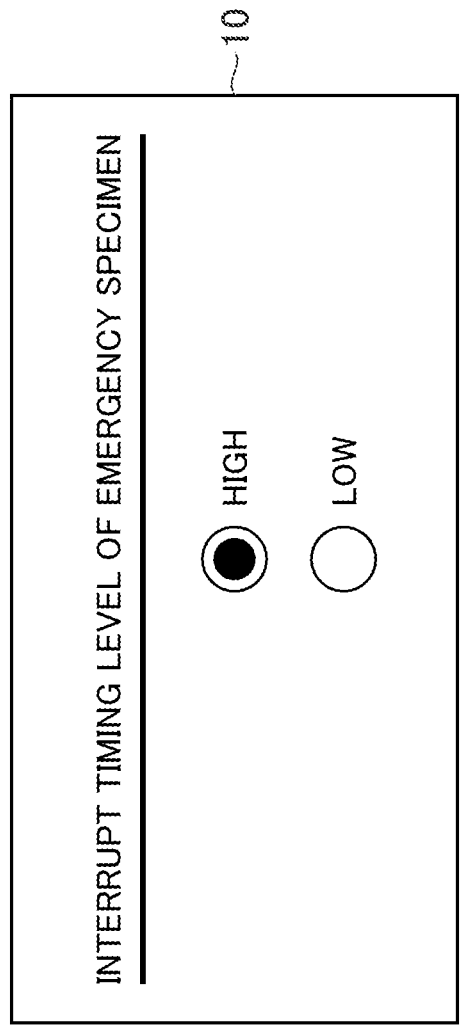
FIG. 13 is a diagram of an outline according to a second embodiment.

It is desirable that an interrupt timing of the urgent specimens is set on the screen. Therefore, as illustrated in FIG. 13, it is desirable that an interrupt timing level of the urgent specimens can be set in two stages of high and low. In the figure, the setting is performed by a radio button method. Alternatively, an interface may be changed according to a screen configuration.

First, the control flow when the interrupt level of the emergency specimen is set to "high" will be described.

When the urgent specimens are inserted into an insertion unit of the urgent specimens, the general specimens being dispensed stops dispensing immediately during dispensing. After the information on a portion where the dispensing is interrupted has been stored in a recording unit of the overall control part 200, the handling of the racks is implemented on the basis of the flowchart of the first embodiment.

As the information stored in the storage unit, for example, at which position of the rack the specimen container has been dispensed, what items have been dispensed, and the like are stored. When the general specimens again return to the dispensing position through the rack standby position 120, the information stored in the storage unit is read out, the remaining dispensing operation of the specimen container whose dispensing has been interrupted is performed, and all the dispensing operations are completed from the specimen containers in the same rack.

Next, a control flow when the interrupt level of the urgent specimens is set to "low" will be described.

When the urgent specimens are inserted into the insertion unit of the urgent specimens, the general specimens being dispensed are dispensed until the dispensing of the racks being dispensed is completed.

After the completion of dispensing, the rack moves to another module if analysis of the specimens is required in another module. When the dispensing of specimens in the rack is finished, the rack is moved to the storage unit. When the general specimen rack is on standby subsequent to this general specimen rack, the rack handling is performed on this rack on the basis of the flowchart of the first embodiment.

As described above, it is desirable that there is provided a screen for setting the interrupt timing of dispensing of the general specimens when an analysis request for the urgent specimens is detected, and the control unit interrupts the dispensing of the general specimens when detecting the analysis request for the urgent specimens on the basis of the set interrupt timing, and allows the general specimens to stand by at the rack standby position under control.

In FIG. 13, the timing level is shown as high or low, but it may be displayed in a unit of dispensing (item unit) or rack unit.

In the present embodiment, the classification on handling of urgent specimens is classified into two categories, but may be classified into more categories according to the target device or the shape or capacity of the specimen racks. For example, as a third type, a specimen container unit can be considered as the timing level "medium".

In this case, all of the specimen containers dispensed when the analysis request for the urgent specimens is detected are completely dispensed, and the other undispensed specimen containers mounted on the rack are not dispensed, and the rack is allowed to stand by at the rack standby position under control. Which specimen containers have been dispensed may be stored in the storage unit of the overall control unit 200 in advance, and when returning to the dispensing position again, the information stored in the storage unit may be read, the dispensing operation may be performed from the undispensed specimen containers, and all the dispensing operation may be completed from the specimen containers in the same rack.

With the implementation of the processing described above, the operation of the urgent specimens can be optimized. More particularly, unwasteful operation can be implemented on the general specimens other than the urgent specimens.

Third Embodiment

Next, a flow of the control when the urgent specimen is inserted into a device to which multiple modules are connected is illustrated in FIGS. 14 to 19.

Figure 14:
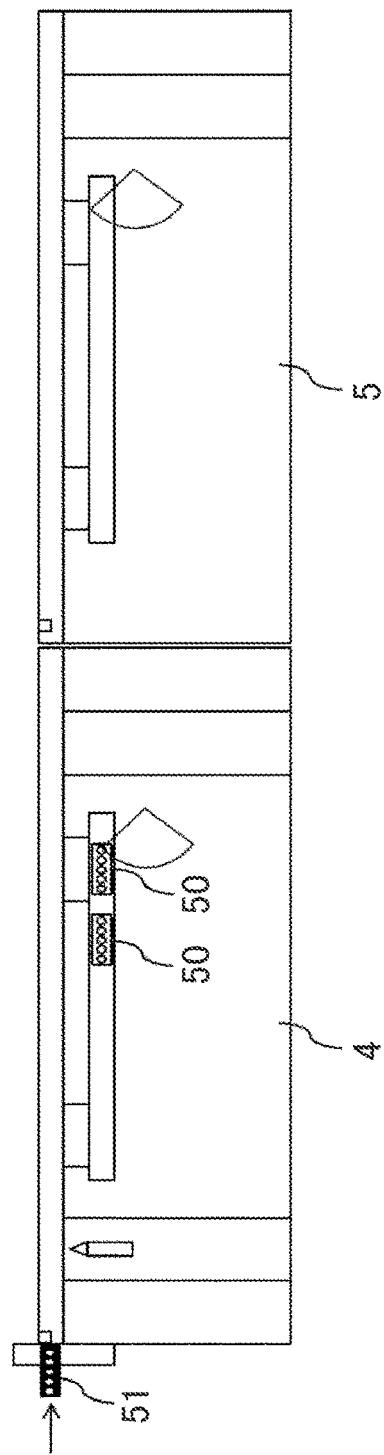
FIG. 14 is a diagram of a schematic control flow according to a third embodiment.

As illustrated in FIG. 14, when the urgent specimen is inserted into a device to which two or more analysis modules are connected, the rack of the general specimens on the sampling line immediately interrupts the dispensing at the same time when a sensor that detects loading senses the loading. Alternatively, the dispensing is interrupted according to the setting of the second embodiment.

In this situation, the progress situation of the interrupted dispensing of the specimens is stored in the storage unit of the overall control unit 200. At the same time, the supply of the general specimen racks from the specimen rack loading unit 1 is interrupted.

Figure 15:
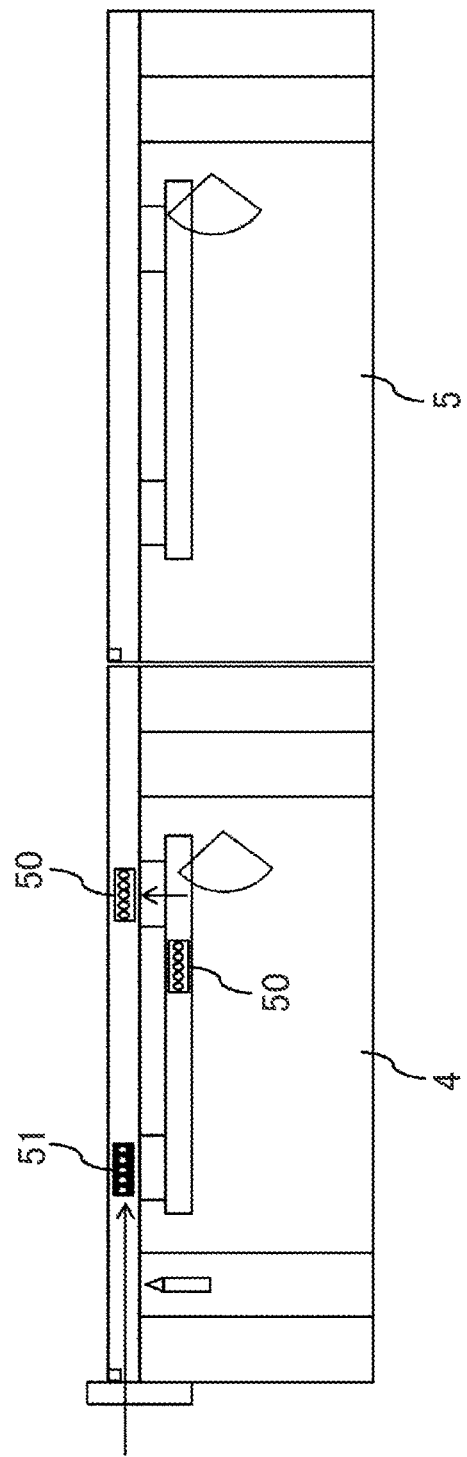
FIG. 15 is a diagram of the schematic control flow according to the third embodiment.

As illustrated in FIG. 15, the general specimens whose dispensing has been interrupted starts to move from the sampling line to the return line.

In the case where the general sample rack whose dispensing has been interrupted at the same time as the movement illustrated in FIG. 15 has been set for an analysis request by another analysis module, the control unit implements the determination of the transport route as to whether the general specimen rack passes through the transport line and again moves to the sampling line after having moved to the transport line, as in the processing method illustrated in the first embodiment, or moves to another analysis module to perform the dispensing in another analysis module.

More specifically, when the urgent specimen is inserted, the general specimen rack on the sampling line is set for the dispensing on another analysis module, and a time until another analysis module with a reservation for dispensing reaches the dispensing position (second dispensing position) is compared with a time until another analysis module again passes through the sampling line and returns to the dispensing position after another analysis module has retreated to the transport line, which is the control method described in the first embodiment. The comparison is performed for each of all the racks on the sampling line at the time when the urgent specimen has been inserted.

Figure 16:
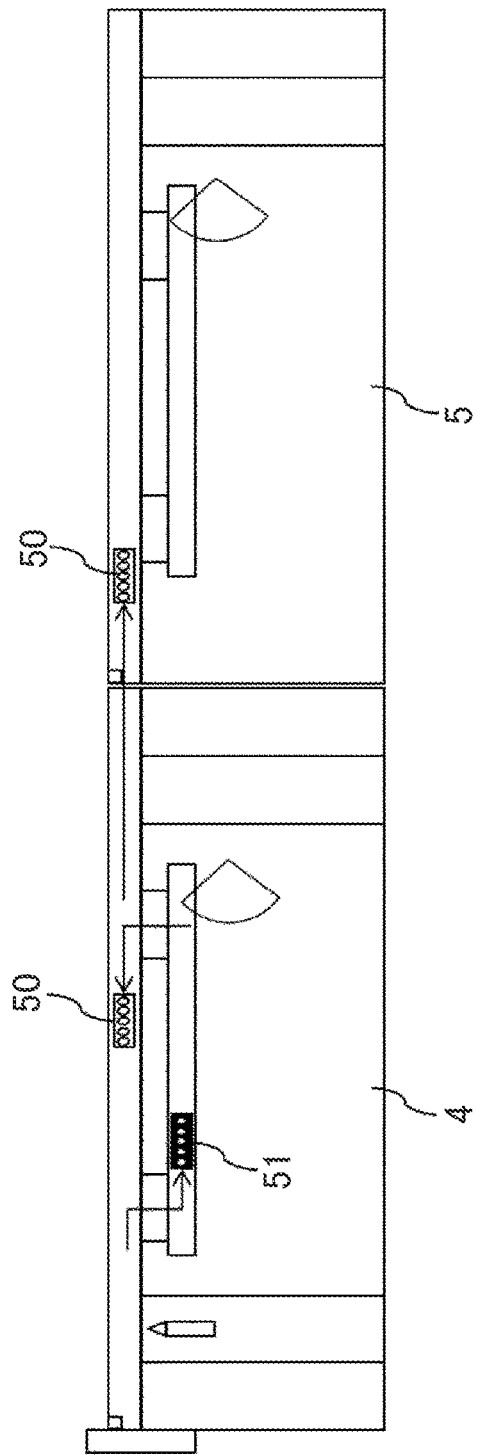
FIG. 16 is a diagram of the schematic control flow according to the third embodiment.
Figure 17:
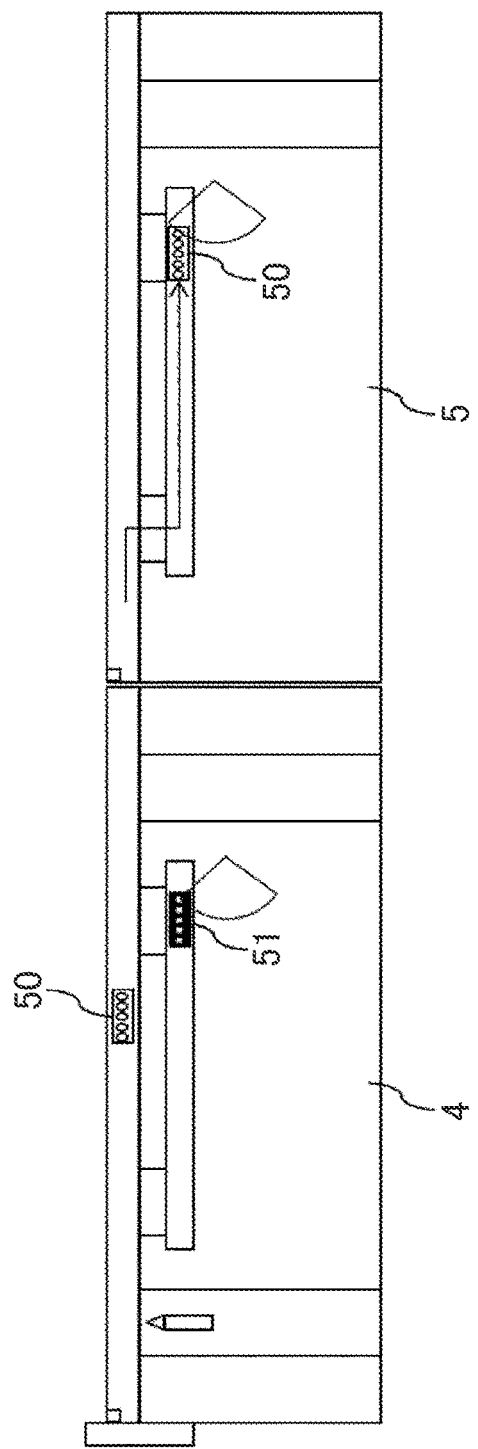
FIG. 17 is a diagram of the schematic control flow according to the third embodiment.

When it is determined that the arrival time when moving to another analysis mode to implement the dispensing is shorter, as illustrated in FIG. 15, after the retreated general specimen rack has been moved onto the transport line, the general specimen rack is moved to another analysis module, and as illustrated in FIGS. 16 and 17, the dispensing set in the moved analysis module is implemented. In FIGS. 15 to 17, one normal specimen rack moves to another analysis module, another normal specimen rack moves in the same manner as the process illustrated in the first embodiment, and the movement between the analysis modules is not performed.

The rack that has completed dispensing set by another analysis module again returns to the original analysis module as illustrated in FIG. 18. Thereafter, as illustrated in FIG. 19, after the rack has moved to the sampling line and waited for the completion of the rack being dispensed earlier, the dispensing is implemented in the same manner as that in normal processing.

As described above, the second sampling line for transporting the racks on the transport line to the second dispensing position at which the specimens are dispensed, and another analysis module that dispenses the specimens from the racks transported to the second dispensing position and analyzes the specimens are provided. When the general specimens are scheduled to be analyzed by another analysis module, the control unit compares the time until the general specimens are again transported to the dispensing position with the time until the general specimens are transported to the second dispensing position. When the time until transporting to the dispensing position is shorter, the general specimens are allowed to stand by at the rack standby position, and when the time until transporting to the second dispensing position is shorter, the general specimens are transported to the second dispensing position under control.

As illustrated in FIGS. 13 to 19, in the case where the multiple analysis modules are connected to each other, when the dispensing previously reserved in another analysis module is first implemented, in addition to the rapid analysis of the urgent specimen, a delay in analysis results of normal samples can be prevented in addition to the rapid analysis of the urgent specimen. In addition, an improvement in the total utilization of the system itself can be expected.

Although the configuration in which two of the same modules are connected has been cited as an example in this example, more analysis modules or a variety of module configurations may be used.

LIST OF REFERENCE SIGNS

1 . . . specimen rack loading unit, 2 . . . ID reading unit, 3 . . . transport line, 4 . . . analysis module, 5 . . . analysis module, 6 . . . analysis module, 7 . . . specimen rack recovery unit, 8 . . . overall management computer (control unit), 9 . . . operation unit, 10 . . . display unit, 20 . . . urgent rack insertion unit, 21 . . . urgent rack detection sensor, 35 . . . analysis unit, 40 . . . recovery unit for analyzed rack, 50 . . . specimen rack (general specimen), 51 . . . specimen rack (urgent specimen), 100 . . . transport line, 101 . . . loading line, 102 . . . return line, 103 . . . sampling line, 110 . . . dispensing device, 111 . . . dispensing position, 120 . . . rack moving mechanism, 121 . . . rack stopping mechanism, 200 . . . general control unit (control unit)

The invention claimed is:

1. An automatic analyzing apparatus comprising:
a transport line that transports a rack on which a sample container containing a sample is mounted, wherein the transport line includes a rack standby position formed between a loading line and a return line;
a sampling line that is parallel to the transport line and transports the rack on the transport line to a dispensing position where the sample is dispensed;
the loading line being perpendicular to the transport line and transferring the rack from the transport line to the sampling line;
an analysis unit that dispenses the sample from the rack transported to the dispensing position and analyzes the sample;
the return line being perpendicular to the transport line and transferring the rack from the sampling line to the transport line;
a control unit that controls the transport line, the sampling line, the loading line and the return line;
wherein the control unit is configured to:
determine a degree of urgency for a first rack located on the sampling line,
determine a degree of urgency for a second rack that is located on the transport line,
upon determination that the degree of urgency for the second rack is greater than the degree of urgency of the first rack, the control unit is further configured to:
unload the first rack from the sampling line onto the transport line through the return line,
store the first rack in the rack standby position on the transport line,
load the second rack from the transport line onto the sampling line through the loading line,
transport the second rack to the dispensing position while the first rack remains in the rack stand by position of the transport line, and
after the second rack is loaded on the sampling line to the dispensing position, load the first rack from the rack standby position to the sampling line through the loading line, and transport the first rack to the dispensing position;
a second sampling line for transporting the rack on the transport line to a second dispensing position for dispensing the sample, and
a second analysis unit that dispenses the sample from the rack transported to the second dispensing position and analyzes the sample,
wherein upon determination that the first rack is scheduled to be analyzed by the second analysis unit, the control unit is further configured to:
compare a time until the first rack is transported to the dispensing position with a time until the first rack is transported to the second dispensing position,
allow the first rack to stand by at the rack standby position upon determination that the time until the first rack is transported to the dispensing position is shorter, and
transport the first rack from the rack standby position to the second dispensing position under control upon determination that the time until the first rack is transported to the second dispensing position is shorter.

2. The automatic analyzing apparatus according to claim 1,
wherein the first rack is a rack located at the dispensing position before scheduled dispensing is completed, and the control unit is further configured to:
interrupt the dispensing of the first rack and allow the first rack to be stored at the rack standby position.

3. The automatic analyzing apparatus according to claim 1, further comprising a screen for setting an interruption timing of the dispensing of the first rack upon detecting the second rack having the greater degree of urgency,
wherein the control unit is further configured to:
interrupt the dispensing of the first rack upon detecting the second rack based on the set interruption timing, and
allow the first rack to stand by at the rack standby position under control.

4. The automatic analyzing apparatus according to claim 1, further comprising a rack stopper for stopping the rack at the rack standby position,
wherein the control unit is further configured to:
control the rack stopper to allow the first rack to be stored at the rack standby position.

5. The automatic analyzing apparatus according to claim 1,
wherein upon determination that a plurality of racks are stored at the rack standby position, the control unit is further configured to:
load each of the plurality of racks onto the sampling line from the rack standby position through the loading line, and
transport each of the plurality of racks to the dispensing position under control, according to a scheduled order of transporting the plurality of racks to the dispensing position on the sampling line under control.

6. The automatic analyzing apparatus according to claim 1,
wherein the first rack is a general specimen rack, and the second rack is an urgent specimen rack.

* * * * *